US012793813B2

(12) United States Patent
Xia et al.

(10) Patent No.: US 12,793,813 B2
(45) Date of Patent: Nov. 10, 2026

(54) METHOD FOR ANALYZING DROPLETS ON THE BASIS OF VOLUME DISTRIBUTION, AND COMPUTER DEVICE AND STORAGE MEDIUM

(71) Applicant: MGI Tech Co., Ltd., Shenzhen (CN)

(72) Inventors: Yun Xia, Shenzhen (CN); Xia Zhao, Shenzhen (CN); Yang Xi, Shenzhen (CN); Yi Wei, Shenzhen (CN); Fang Chen, Shenzhen (CN); Hui Jiang, Shenzhen (CN)

(73) Assignee: MGI Tech Co., Ltd., Shenzhen (CN)

( * ) Notice: Subject to any disclaimer, the term of this patent is extended or adjusted under 35 U.S.C. 154(b) by 539 days.

(21) Appl. No.: 18/272,128

(22) PCT Filed: Jan. 13, 2021

(86) PCT No.: PCT/CN2021/071432

§ 371 (c)(1),
(2) Date: Jul. 13, 2023

(87) PCT Pub. No.: WO2022/151025

PCT Pub. Date: Jul. 21, 2022

(65) Prior Publication Data

US 2024/0120030 A1 Apr. 11, 2024

(51) Int. Cl.
*G16B 40/10* (2019.01)
*C12Q 1/6851* (2018.01)
*G01N 21/85* (2006.01)

(52) U.S. Cl.
CPC ............. *G16B 40/10* (2019.02); *G01N 21/85* (2013.01); *C12Q 1/6851* (2013.01); *G01N 2021/8564* (2013.01)

(58) Field of Classification Search
None
See application file for complete search history.

(56) References Cited

U.S. PATENT DOCUMENTS

| | | | | |
|---|---|---|---|---|
| 9,395,387 | B1 * | 7/2016 | Ohta | G01Q 10/065 |
| 2006/0278530 | A1 * | 12/2006 | Sasaki | G01N 21/6458<br>204/452 |

(Continued)

FOREIGN PATENT DOCUMENTS

| | | |
|---|---|---|
| CN | 102405402 | 4/2012 |
| CN | 107502660 | 12/2017 |

OTHER PUBLICATIONS

Hand, Mannila, and Smyth, "Principle of Data Mining", MIT Press 2001 (Year: 2001).*

(Continued)

*Primary Examiner* — Shelby A Turner
*Assistant Examiner* — Cynthia L Davis
(74) *Attorney, Agent, or Firm* — ScienBiziP, P.C.

(57) ABSTRACT

The present application provides a method for analyzing droplets on the basis of volume distribution including obtaining a total volume V of a sample containing target molecules based on a system prepared using the sample. The system is emulsified into droplets. A droplet system is obtained when the droplets obtaining the sample executes an amplification reaction. A droplet image of the droplet system is obtained. A total number n of droplets included in the droplet system is obtained based on the droplet image. A droplet volume distribution of the droplet system is obtained based on the droplet image. A number j of negative droplets among the n droplets is counted. A quantitative analysis is performed for the target molecules according to the total volume V of the sample, the total number n of droplets, the droplet volume distribution information, and the number j of negative droplets.

3 Claims, 8 Drawing Sheets

(56) References Cited

U.S. PATENT DOCUMENTS

| | | | | |
|---|---|---|---|---|
| 2012/0224050 | A1* | 9/2012 | Staker | G01N 21/6452 348/95 |
| 2017/0175174 | A1* | 6/2017 | Chiu | C12Q 1/6816 |
| 2022/0008928 | A1* | 1/2022 | Colston, Jr. | G01N 21/49 |

OTHER PUBLICATIONS

Kosir, Divieto, Pavsic, Pavarelli, Dobnik, Dreo, Belotti, Sassi, and Zel, Droplet Volume Variability as a critical factor for accuracy of absolute quantification using droplet digital PCR, Analytical and Bioanalytical Chemistry, 2017 (Year: 2017).*

Toan Huynh et al.; "General methods for quantitative interpretation of results of digital variable-volume assays" ; Analyst;Oct. 24, 2019; vol. 2019, No. 144, pp. 7209-7219.

Nivedita, Majumdar, et al.; "Poisson Plus Quantification for Digital PCR Systems"; Scientific Reports;Aug. 29, 2017; vol. 7, No. 9617, pp. 1-10.

* cited by examiner

METHOD FOR ANALYZING DROPLETS ON THE BASIS OF VOLUME DISTRIBUTION, AND COMPUTER DEVICE AND STORAGE MEDIUM

FIELD

The present application relates to the technical field of biological information analysis and biochemical detection, in particular to a method for analyzing droplets based on volume distribution, a computer device and a storage medium.

BACKGROUND

Polymerase chain reaction (PCR) is an important method for rapid replication of target nucleic acid molecules in vitro or in test tubes, which can be used to amplify specific DNA fragments for qualitative and quantitative detection of biochemical analytes such as nucleic acids. Digital PCR (dPCR) is an improved method for quantitative detection in traditional PCR technology, in which the sample containing the template (i.e., the target molecules) is diluted to a certain ratio, and the template is randomly dispersed to several dozens to millions of reaction partitions by physical partitioning. The signals of each partition at the end of the reaction are collected and processed, and finally the statistical analysis is completed by direct counting or Poisson distribution principle to calculate the content and concentration of the template to be measured in the sample. Physical partitioning in digital PCR is mainly divided into two forms: droplet partitioning and solid phase partitioning, among which droplet digital PCR (ddPCR) based on droplet partitioning has developed into the mainstream form of digital PCR commercial products, such as Bio-Rad, Stilla, Raindance and other manufacturers have launched core products based on related technologies, such as QX200™, Naica™, RainDrop™, etc.

Random emulsified droplet digital PCR is a special form of droplet digital PCR. It uses simple driving methods such as mechanical oscillation to simplify the droplet partitioning of samples, and forms droplets with a random total number and each droplet has a random size and volume. This method gets rid of the dependence of digital PCR technology on microfluidic systems or solid-phase microchips, and has technical advantages such as low cost, easy operation, less space occupation, low detection load, wide dynamic range, and high detection throughput. However, the current quantitative model and calculation method of random emulsified droplet digital PCR needs to measure the exact volume of each droplet one by one. If the accuracy or precision of the measurement data is insufficient, the measurement data will cause large errors in the quantitative calculation results. Therefore, the analysis method of random emulsified droplet digital PCR puts forward higher technical requirements for optical detection equipment and supporting image processing algorithms, and often needs to rely on more complex optical system (such as confocal microscopy system or light-sheet fluorescence microscopy system) to obtain continuous profile image data of each droplet, and then reconstruct the droplets in three dimensions through image processing algorithm to obtain accurate volumes, which undoubtedly adds additional hardware and software costs to this method. Therefore, there is an urgent need for a new quantitative analysis method that can effectively overcome these technical drawbacks, eliminate the dependence on accurate measurement of droplet volumes, simplify the software and hardware system and operation process of random emulsified droplet digital PCR, and lower user costs.

SUMMARY

In view of the above, it is necessary to propose a method for analyzing droplets based on volume distribution, a computer device and a storage medium, which can simplify the existing quantitative model based on random emulsified droplets, eliminate the reliance on measurement of exact volume of each droplet, and improve computational efficiency while reducing costs of technology-related hardware and software.

The first aspect of the present application provides a method based on volume distribution analysis of droplets. The method includes the following steps: preparing a system to be emulsified using a sample containing target molecules, and obtaining a total volume V of the sample containing the target molecules; emulsifying the system into droplets, subjecting the droplets to conditions and operations for performing amplification reactions, causing the droplets containing the sample to undergo amplification reactions and obtaining a droplet system; acquiring a droplet image of the droplet system, and obtaining a total number n of droplets comprised in the droplet system based on the droplet image; obtaining a droplet volume distribution of the droplet system based on the droplet image; counting a number j of negative droplets or a number n-j of positive droplets among the n droplets; and performing a quantitative analysis for the target molecules according to the total volume V of the sample containing the target molecules, the total number n of droplets, the droplet volume distribution, and the number j of negative droplets or the number n-j of positive droplets.

A second aspect of the present application provides a computer device, including: a storage device and a processor, the storage device storing at least one computer-readable instruction, the processor executing the at least one computer-readable instruction to perform the following steps: obtaining a total volume V of a sample containing target molecules; acquiring a droplet image of a droplet system, and obtaining a total number n of droplets comprised in the droplet system based on the droplet image, wherein the droplet system is obtained by preparing a system to be emulsified using the sample containing target molecules; emulsifying the system into droplets; subjecting the droplets to conditions and operations for performing amplification reactions, causing the droplets containing the sample to undergo amplification reactions; obtaining a droplet volume distribution of the droplet system based on the droplet image; counting a number j of negative droplets or a number n-j of positive droplets among the n droplets; and performing a quantitative analysis for the target molecules according to the total volume V of the sample containing the target molecules, the total number n of droplets, the droplet volume distribution, and the number j of negative droplets or the number n-j of positive droplets.

A third aspect of the present application provides a non-transitory storage medium having at least one computer-readable instruction stored thereon. When the at least one computer-readable instruction is executed by a processor, the following steps are performed: obtaining a total volume V of a sample containing target molecules; acquiring a droplet image of a droplet system, and obtaining a total number n of droplets comprised in the droplet system based on the droplet image, wherein the droplet system is obtained by preparing a system to be emulsified using the sample containing target molecules; emulsifying the system into droplets; subjecting the droplets to conditions and operations for performing amplification reactions, causing the droplets containing the sample to undergo amplification reactions; obtaining a droplet volume distribution of the droplet system based on the droplet image; counting a number j of negative droplets or a number n-j of positive droplets among the n droplets; and performing a quantitative analysis for the target molecules according to the total volume V of the sample containing the target molecules, the total number n of droplets, the droplet volume distribution, and the number j of negative droplets or the number n-j of positive droplets.

The method for analyzing droplets based on volume distribution, a computer device and a storage medium, which can simplify the existing quantitative model based on random emulsified droplets, eliminate the reliance on measurement of exact volume of each droplet, and improve computational efficiency while reducing costs of technology-related hardware and software.

BRIEF DESCRIPTION OF THE DRAWINGS

In order to more clearly describe the technical solutions in the embodiments of the present disclosure or the prior art, the following briefly introduces the drawings that need to be used in the description of the embodiments or the prior art. Obviously, the drawings in the following description are only embodiments of the present disclosure. For those of ordinary skill in the art, other drawings can be obtained according to the provided drawings without creative work.

The following specified implementations will further illustrate the embodiments of the present disclosure in conjunction with the above-mentioned drawings.

DETAILED DESCRIPTION

In order to be able to understand the object, features and advantages of the embodiments of the present disclosure, implementations of the disclosure will now be described, by way of embodiments only, with reference to the drawings. It should be noted that non-conflicting details and features in the embodiments of the present disclosure may be combined with each other.

In the following description, specific details are explained in order to make the embodiments of the present disclosure understandable. The described embodiments are only a portion of, rather than all of the embodiments of the present disclosure of them. Based on the embodiments of the present disclosure, other embodiments obtained by a person of ordinary skill in the art without creative work shall be within the scope of the present disclosure.

Unless otherwise defined, all technical terms used herein have the same meaning as commonly understood by one of ordinary skill in the art. The technical terms used herein are not to be considered as limiting the scope of the embodiments.

Figure 1:
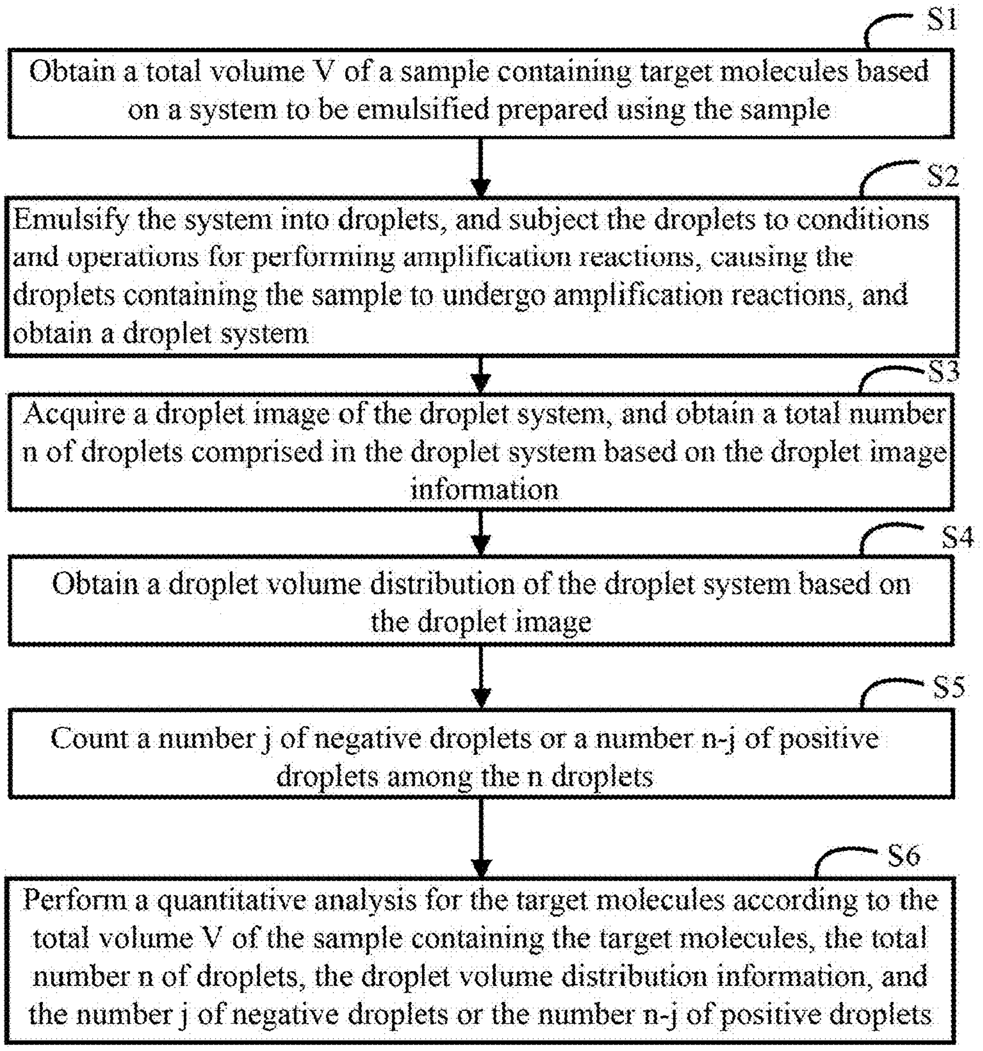
FIG. 1 schematically shows a flowchart of a droplet analysis method provided by one embodiment of the present application.

FIG. 1 is a flowchart of a droplet analysis method provided by a preferred embodiment of the present application.

Figure 13:
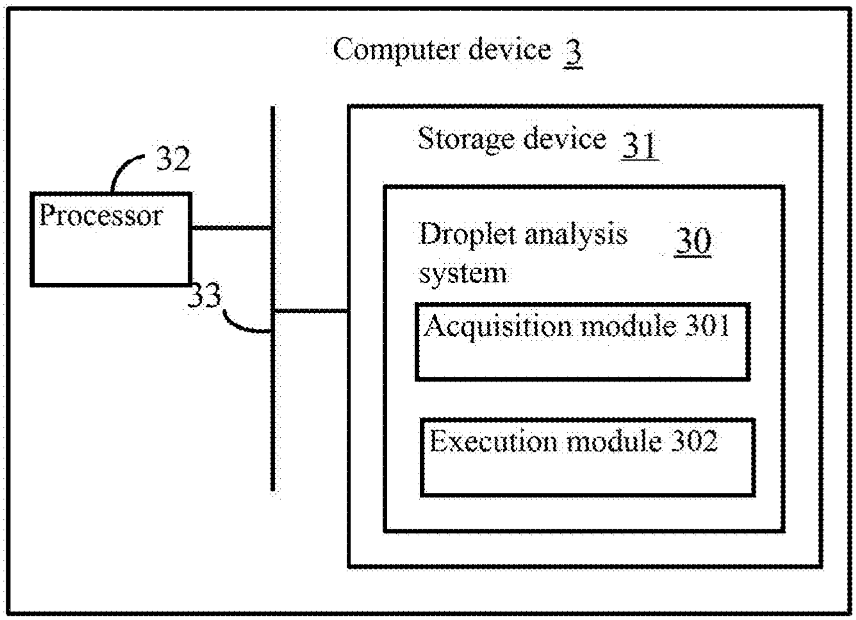
FIG. 13 is a diagram of an operating environment of a droplet analysis system provided by the preferred embodiment of the present application.

In this embodiment, the droplet analysis method can be applied to a computer device (such as a computer device 3 shown in FIG. 13). For a computer device that needs to perform the droplet analysis method, a function provided by the droplet analysis method may be directly integrated on the computer device or run on the computer device in a form of a software development kit (SDK).

As shown in FIG. 1, the droplet analysis method includes following blocks. According to different requirements, an order of the blocks in the flow chart can be changed, and some blocks can be omitted.

Block S1, a sample containing target molecules is used to prepare a system to be emulsified, and a total volume V of the sample containing the target molecules is obtained.

In one embodiment, the target molecules may be biomolecule such as nucleic acid, protein, polysaccharide, metal ion, and small molecule, etc. In one embodiment, when the sample containing the target molecules are used to prepare the system to be emulsified, the total volume V of the sample containing the target molecules can be determined according to a reading of a pipette. In one embodiment, the computer device can obtain the total volume V of the system containing the target molecules in response to user input. For example, a user can manually enter the total volume V of the target molecules containing system according to the reading of the pipette.

Block S2, the system to be emulsified is emulsified into droplets, conditions and operations required for an execution of an amplification reaction are performed on the droplets, so that a droplet system is obtained when the droplets containing the sample fully complete the amplification reaction.

Specifically, emulsified oil and an emulsifier premix can be added into the system to be emulsified, so that the system to be emulsified is randomly emulsified into the droplets in the presence of the emulsifier premix, and the droplets are provided conditions and operations required for the execution of the amplification reaction of nucleic acid, so that the droplets containing the target molecules perform the amplification reaction to obtain the droplet system.

Block S3, the computer device acquires droplet image of the droplet system, and obtains a total number n of droplets included in the droplet system based on the droplet image.

In one embodiment, before obtaining the total number n of droplets based on the droplet image, a process performed on the droplet image may include, but not limited to, reconstruction, splicing, correction, enhancement, noise reduction, registration etc.

In one embodiment, a method described in PCT/CN2020/075309 can be used to obtain the droplet image of the droplet system, and process the droplet image to obtain the total number n of droplets included in the droplet system.

In one embodiment, the acquiring of the droplet image of the droplet system includes: respectively exciting indicator dyes corresponding to different wavelengths in the droplet system by using a preset method under conditions of dual/multi-channel wavelengths, and obtaining the droplet image of the droplet system by taking fluorescent images of the channel corresponding to each indicator dye.

Specifically, at least two indicator dyes at a specific concentration can be added when preparing the system to be emulsified. The at least two indicator dyes respectively correspond to different wavelengths of excitation. The at least two indicator dyes include a working dye and a reference dye.

Specifically, the preset method can be used to respectively excite the working dye and the reference dye in the droplet system under the conditions of dual/multi-channel wavelengths, take fluorescent images of the channel corresponding to the working dye, and take fluorescent images of the channel corresponding to the reference dye, thereby the droplet image of the droplet system is obtained.

In one embodiment, the preset method includes, but is not limited to, a serial reading method, a plane scanning method or a continuous profiling three-dimensional reconstruction method.

Block S4, the computer device obtains droplet volume distribution of the droplet system based on the droplet image.

In one embodiment, the droplet volume distribution of the droplet system includes, but is not limited to, a droplet volume cumulative distribution function, a droplet volume probability density function, and/or an expectation and a variance of a droplet volume distribution.

In a first embodiment, the obtaining the droplet volume distribution of the droplet system based on the droplet image includes (a1)-(a7):

(a1) Determining a smallest droplet and a largest droplet from the n droplets based on the droplet image.

In the first embodiment, the determining the smallest droplet and the largest droplet from the n droplets includes (a11)-(a12):

(a11) Based on the droplet image, determining a number of pixels included in each of the n droplets according to boundary position.

In this embodiment, the boundary position refers to edge coordinates of each droplet, specifically, the edge coordinates of each droplet can be obtained by using an image edge extraction algorithm.

In this embodiment, by traversing all pixels of an image, a total number of pixels falling within a range of edge coordinates of a certain droplet can be taken as the total number of pixels of the certain droplet. The certain droplet can be any droplet in the n droplets.

(a12) Sorting the n droplets according to the number of pixels included in each droplet, taking a droplet with the fewest pixels as the smallest droplet, and taking a droplet with the most pixels as the largest droplet.

In a second embodiment, the determining the smallest droplet and the largest droplet from the n droplets includes (a111)-(a112):

(a111) Based on the droplet image, determining spatial coordinates and boundary position of each of the n droplets in a space coordinate system, and determining, according to the spatial coordinates and boundary position of each droplet, a minimum point and a maximum point of each droplet in the space coordinate system, calculating a boundary range of each droplet based on the minimum point and the maximum point corresponding to each droplet.

In one embodiment, the spatial coordinate system may be a one-dimensional coordinate system, a two-dimensional coordinate system, or a three-dimensional coordinate system.

In one embodiment, tomographic profile scanning may be performed for the droplet image to reconstruct three-dimensional coordinates. The boundary position refers to the edge coordinates of each droplet, which can be obtained using an image edge extraction algorithm.

The minimum point of each droplet refers to a minimum value of a certain dimension (such as longitude) of the edge coordinates of each droplet. Correspondingly, the maximum point of each droplet refers to a maximum value of the certain dimension of the edge coordinates of each droplet. The boundary range of each droplet is a value obtained by subtracting the minimum value from the maximum value of each droplet.

(a112) Sorting the n droplets according to the boundary range of each droplet, taking a droplet with a smallest boundary range as the smallest droplet, and taking a droplet with a largest boundary range as the largest droplet.

(a2) Acquiring a volume of the smallest droplet and a volume of the largest droplet.

In one embodiment, the volume of the smallest droplet may be obtained according to a total number of pixels in a region occupied by the smallest droplet in the droplet image and a predetermined image pixel length conversion ratio.

Likewise, the volume of the largest droplet can be obtained according to the total number of pixels in the region occupied by the largest droplet in the droplet image and a predetermined conversion ratio of image pixel length.

In one embodiment, the method for determining the conversion ratio of image pixel length includes: capturing an image of a preset square using a microscope under a preset magnification of the microscope; calculating a total number of pixels included in a side length of the preset square in the captured image; and calculating the conversion ratio of the image pixel length based on the calculated total number of pixels included in the side length of the preset square and an actual side length of the preset square.

For example, assuming that the total number of pixels included in the side length of the preset square in the captured image is 1150 pixels, and the actual length of the side length of the preset square is 2 mm, then the conversion ratio of the image pixel length is 1.73660264 μm/pixel.

It should be noted that the preset magnification refers to a magnification used when the microscope captures the droplet image.

(a3) Obtaining a droplet volume distribution interval by taking the volume of the smallest droplet as an upper boundary and taking the volume of the largest droplet as a lower boundary.

(a4) Dividing the droplet volume distribution interval into a preset number of subintervals according to a preset division method.

(a5) Judging the subintervals into which each of the n droplets falls.

(a6) Obtaining a droplet volume frequency distribution of the droplet system by counting a number of droplets falling into each of the subintervals of the preset number of subintervals, and obtaining the expectation and the variance of the droplet volume distribution of the droplet system according to the droplet volume frequency distribution of the droplet system.

Figure 2:
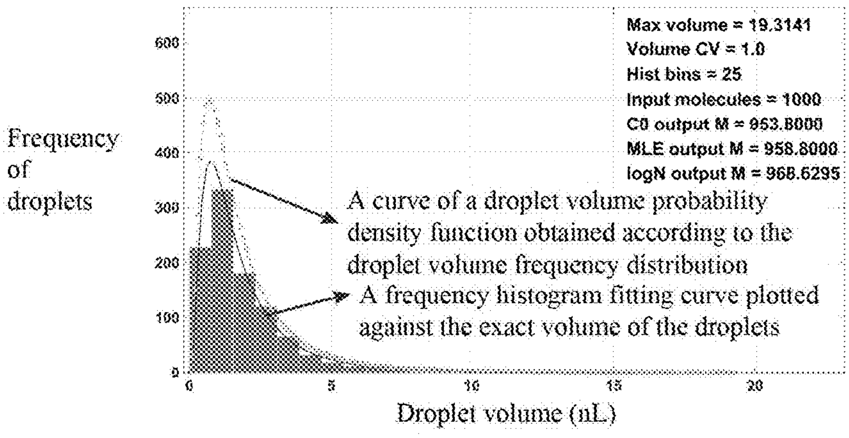
FIG. 2 shows a schematic diagram of a principle of a droplet volume frequency segmentation method.

(a7) Obtaining the droplet volume probability density function of the droplet system based on the expectation and the variance of the droplet volume distribution of the droplet system (for example, refer to FIG. 2).

In one embodiment, the preset division method can be a method of an average segmentation, a method of a logarithmic segmentation, a method of an artificial segmentation, and the like.

In order to clearly illustrate the present application, the preset division method refers to the method of the average segmentation as an example below.

Figure 3:
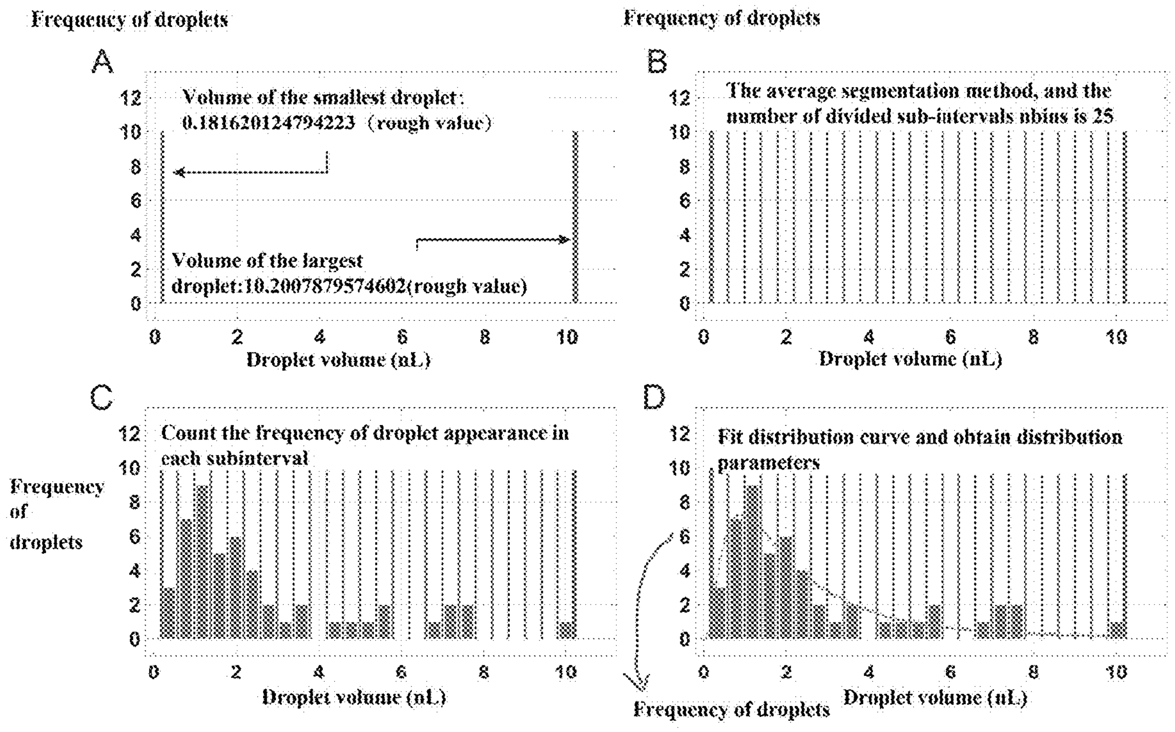
FIG. 3 illustrates a division of the droplet volume distribution interval according to an average segmentation method.

For example, among 50 droplets formed by emulsification, the volume of the smallest droplet is 0.182 (rough value), and the volume of the largest droplet is 10.201 (rough value), so the droplet volume distribution interval is determined to be [0.182,10.201](refer to A as shown in FIG. 3). Assume that the preset number nbins is set to 25, and the division method is set to be the average segment (refer to B as shown in FIG. 3), so the droplet volume distribution interval [0.182, 10.201] can be equally divided into 25 subintervals, namely

| | | |
|---|---|---|
| ([0.181620124794223 | 0.582386838100861 | 0.983153551407499 |
| 1.38392026471414 | 1.78468697802078 | 2.18545369132741 |
| 2.58622040463405. | 2.98698711794069 | 3.38775383124733 |
| 3.78852054455397 | 4.18928725786061 | 4.59005397116724 |
| 4.99082068447388 | 5.39158739778052 | 5.79235411108716 |
| 6.19312082439380 | 6.59388753770043 | 6.99465425100707 |
| 7.39542096431371 | 7.79618767762035 | 8.19695439092699 |
| 8.59772110423362 | 8.99848781754026 | 9.39925453084690 |
| 9.80002124415354 | 10.2007879574602]). | |

It should be noted that, the smaller the value of the preset number nbins is set, the higher the degree of simplification, and the lower the dependence on the precise of the volume data of the droplet; otherwise, the higher.

Then, according to the droplet image or droplet sorting result, a frequency of droplets occurred in each subinterval is counted (refer to C shown in FIG. 3), so that each droplet is classified. Finally, according to the droplet volume frequency distribution obtained by statistics [that is, an average volume value of each subinterval (the average volume value of each subinterval is a sum of volume values corresponding an upper boundary and a lower boundary of each subinterval divided by 2, such as an average volume value of a first subinterval is a sum of 0.181620124794223 and 0.582386838100861 divided by 2, and equals 0.382003481447542):

| | | |
|---|---|---|
| [0.382003481447542 | 0.782770194754180 | 1.18353690806082 |
| 1.58430362136746 | 1.98507033467409 | 2.38583704798073 |
| 2.78660376128737 | 3.18737047459401 | 3.58813718790065 |
| 3.98890390120729 | 4.38967061451392 | 4.79043732782056 |
| 5.19120404112720 | 5.59197075443384 | 5.99273746774048 |
| 6.39350418104712 | 6.79427089435375 | 7.19503760766039 |
| 7.59580432096703 | 7.99657103427367 | 8.39733774758031 |
| 8.79810446088694 | 9.19887117419358 | 9.59963788750022 |
| 10.0004046008069] | | |

and frequency values: (3 7 9 5 6 4 2 1 2 0 1 1 1 2 0 0 1 2 2 0 0 0 0 0 1)], according to a designed distribution model such as a logarithmic normal distribution, the frequency distribution is fitted (such as least squares fitting), so as to determine a fitting curve of the droplet volume probability density function $f(v)$ and the corresponding distribution parameters (such as an expectation E[v] and a variance D(v) of the droplet volume distribution (refer to D shown in FIG. 3).

It should be noted that a frequency at which droplets appear in each subinterval is also the number of droplets falling into each subinterval. A frequency value refers to the number of droplets falling into each subinterval.

In order to clearly illustrate the present application, the preset division method refers to logarithmic segmentation as an example below.

Figure 4:
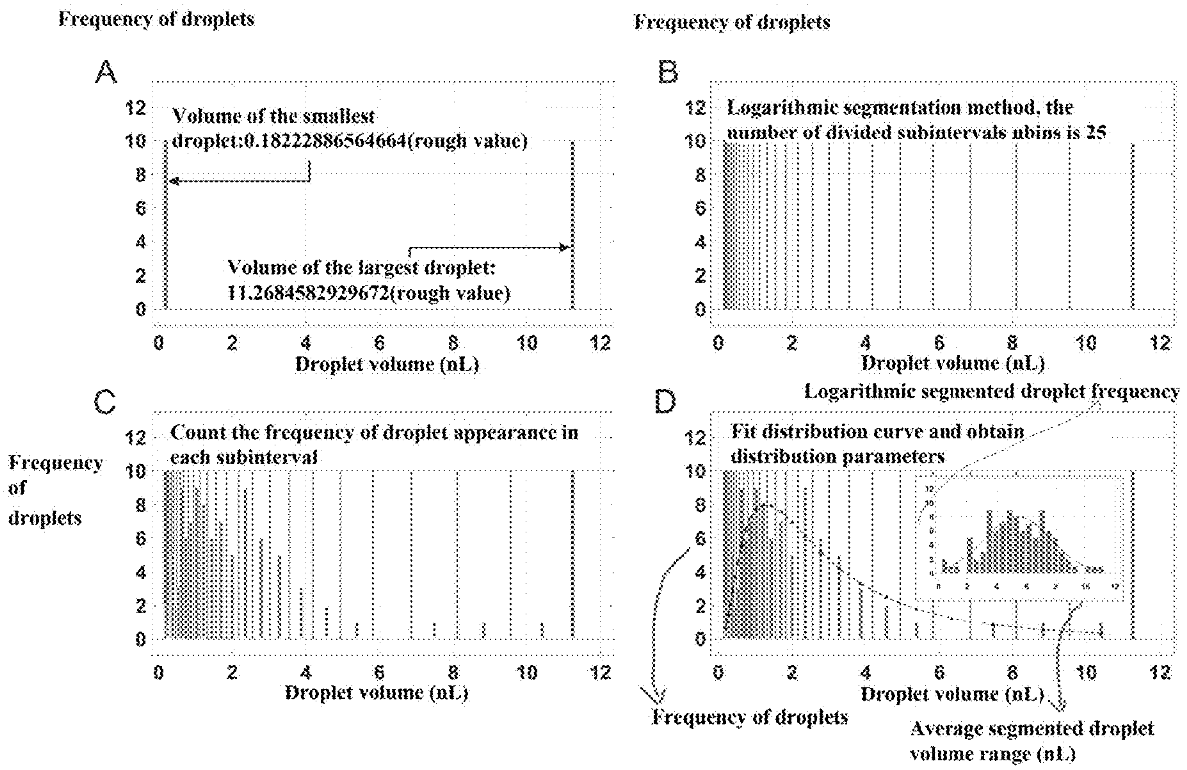
FIG. 4 illustrates a division of the droplet volume distribution interval according to a logarithmic segmentation method.

For example, among 100 droplets formed by emulsification, the smallest droplet volume is 0.182 (rough value), and the largest droplet volume is 11.268 (rough value), so the droplet volume distribution interval is determined to be [0.182, 11.268](refer to A as shown in FIG. 4). Assume that the preset number nbins is set to 25, and the division method is set to be the logarithmic segmentation (refer to B as shown in FIG. 4), so the droplet volume distribution interval [0.182, 11.268] is equally divided into 25 subintervals, that is

| | | |
|---|---|---|
| ([0.182228865646640 | 0.214915166666512 | 0.253464393247437 |
| 0.298928175432033 | 0.352546773620747 | 0.415782913105351 |
| 0.490361687485880 | 0.578317619543623 | 0.682050163399508 |
| 0.804389162067032 | 0.948672046093918 | 1.11883487928573 |
| 1.31951973525569 | 1.55620133405279 | 1.83533639353897 |
| 2.16453976984856 | 2.55279219207428 | 3.01068525822066 |
| 3.55071037595975 | 4.18759953054656 | 4.93872717610593 |
| 5.82458421395988 | 6.86933698821166 | 8.10148654808992 |
| 9.55464616185163 | 11.2684582929672]). | |

As mentioned above, the smaller the value of the preset number nbins is set, the higher the degree of simplification, and the lower the dependence on the precise of the volume data of the droplets; otherwise, the higher.

Then, according to the droplet image or droplet sorting result, the frequency of droplets occurrence in each subinterval is counted (refer to C as shown in FIG. 4), so as to classify each droplet. Finally, according to the droplet volume frequency distribution obtained by statistics [that is, the average volume value of each subinterval:

| | | |
|---|---|---|
| [0.198572016156576 | 0.234189779956975 | 0.276196284339735 |
| 0.325737474526390 | 0.384164843363049 | 0.453072300295616 |
| 0.534339653514752 | 0.630183891471566 | 0.743219662733270 |
| 0.876530604080475 | 1.03375346268983 | 1.21917730727071 |
| 1.43786053465424 | 1.69576886379588 | 1.99993808169377 |
| 2.35866598096142 | 2.78173872514747 | 3.28069781709020 |
| 3.86915495325316 | 4.56316335332624 | 5.38165569503291 |
| 6.34696060108577 | 7.48541176815079 | 8.82806635497077 |
| 10.4115522274094] | | |

and the frequency values: (2 1 1 0 5 2 3 9 6 7 9 8 6 7 5 9 6 5 3 2 1 0 1 1 1)], the frequency distribution is fitted (such as least squares fitting) according to a designed distribution model (such as the lognormal distribution), so as to determine the fitting curve of the droplet volume probability density function $f(v)$ and the corresponding distribution parameters (such as an expectation $E[v]$ and a variance $D(v)$ of the droplet volume distribution) (refer to D shown in FIG. 4).

In a second embodiment, the obtaining the droplet volume distribution of the droplet system based on the droplet image includes (b1)-(b6):

(b1) Acquiring a volume of each droplet based on the droplet image, and sorting the n droplets according to the volume of each droplet.

Specifically, the volume of each droplet may be obtained by using the method for obtaining the volume of the largest droplet and the volume of the smallest droplet above.

(b2) Dividing the n droplets into t groups based on an arrangement sequence of the n droplets.

In one implementation, each of the t groups includes the same number of droplets.

(b3) Obtaining t volume values by obtaining a volume value of a largest droplet or obtaining a volume value of a smallest droplet in each of the t groups.

For example, selecting the volume value of the largest droplet in each of the t groups to obtain the t volume values; or selecting the volume value of the smallest droplet in each of the t groups to obtain the t volume values.

(b4) Determining a quantile q based on the t, and obtaining a plurality of estimated values of expectation $\mu$ and a plurality of estimated values of variance $\sigma^2$ based on the quantile q and the t volume values.

(b5) Based on a preset evaluation function (such as least squares fitting), selecting a best estimated value of the expectation $\mu$ from the plurality of estimated values of the expectation $\mu$, and selecting a best estimated value of the variance $\sigma^2$ from the plurality of estimated values of the variance $\sigma^2$.

The best estimated value of the expectation $\mu$ and the best estimated value of the variance $\sigma^2$ are extremums of the preset evaluation function or values closest to the extremums.

(b6) According to characteristics of the lognormal distribution, the droplet volume probability density function $f(v)$ of the droplet system is obtained based on the best estimated value of the expectation $\mu$ and the best estimated value of the variance $\sigma^2$.

Figure 5:
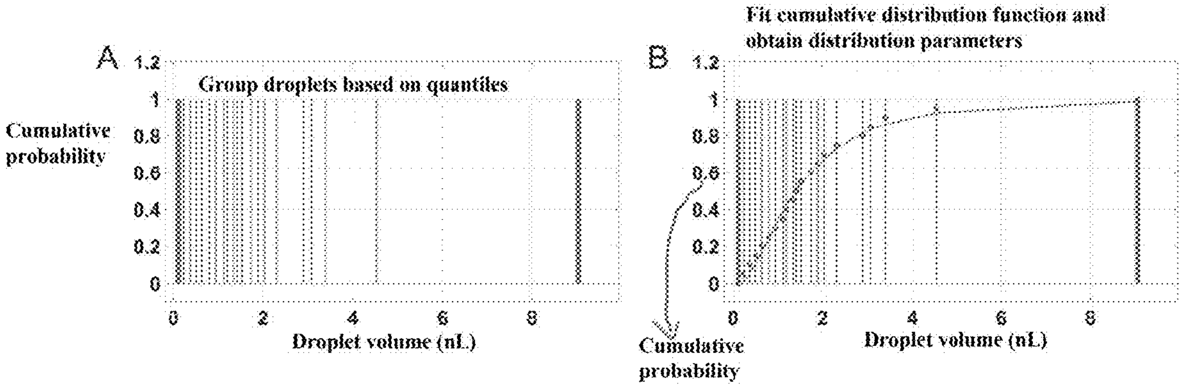
FIG. 5 illustrates grouping droplets according to quantiles, and the acquisition of distribution parameters.

In order to clearly illustrate the present application, for example, 100 droplets are formed by emulsification, and after sorting the 100 droplets according to the volume from small to large, the 100 droplets are divided into 20 groups according to each group of 5 droplets (i.e. t=20), thus a first group includes first 5 droplets, a second group includes the 6th to 10th droplets, and a third group includes the 11th to 15th droplets, and so on, the last group includes the 96th to 100th droplets (refer to A as shown in FIG. 5). Assume that the droplet volume cumulative distribution function is $F(v)$, and the distribution is known to be the lognormal distribution with unknown parameters expectation $\mu$ and variance $\sigma^2$. The volume value of the largest droplet in each group is obtained, for example, a total of 20 volume values is obtained from 20 groups:

| | | |
|---|---|---|
| ([0.234639012177894 | 0.376927442027653 | 0.507218999309542 |
| 0.643287864899695 | 0.809041890157066 | 0.947884106383989 |
| 1.12382040271824 | 1.20507397594139 | 1.34211418799552 |
| 1.41492736480395 | 1.52320627555393 | 1.73918071258546 |
| 1.89304203055652 | 2.03130953049959 | 2.30718858922129 |
| 2.89314023492847 | 3.07195764782807 | 3.39530633902546 |
| 4.53002815195639 | 9.04949424726351]) | |

Record these 20 volume values as $v_{q_{0.05}}, v_{q_{0.10}}, v_{q_{0.15}}, \ldots, v_{q_{1.00}}$, where q is the quantile, the following equations are obtained for the quantile q and the droplet volume cumulative distribution function $F(v)$:

$$F(v_{q_{0.05}};\mu,\sigma^2)=0.05 \quad \text{(First equation)}$$

$$F(v_{q_{0.10}};\mu,\sigma^2)=0.10 \quad \text{(Second equation)}$$

$$F(v_{q_{0.15}};\mu,\sigma^2)=0.15 \quad \text{(Third equation)}$$

$$\ldots,\ldots,\ldots,\ldots,\ldots, \quad \text{(Fourth equation to nineteenth equation)}$$

$$F(v_{q_{1.00}};\mu,\sigma^2)=1.00 \quad \text{(Twentieth equation)}$$

By solving the first to twentieth equations, a plurality of estimated values of expectation $\mu$ and a plurality of estimated values of variance $\sigma^2$ can be obtained (refer to B as shown in FIG. 5). Then use a preset evaluation function such as least squares fitting to select the best estimated value of the expectation $\mu$ from the plurality of estimated values of the expectation $\mu$, and select the best estimate value of variance $\sigma^2$ from the plurality of estimated values of variance $\sigma^2$. For example, s and $\sigma^2$ can be used as the best estimated value of expectation s and the best estimated value of variance $\sigma^2$ respectively by solving the following residual square sum SSE to obtain a minimum value:

$$SSE=[F(v_{q_{0.10}};\mu,\sigma^2)-0.10]^2+[F(v_{q_{0.15}};\mu,\sigma^2)-0.15]^2+\ldots+[F(v_{q_{1.00}};\mu,\sigma^2)-1.00]^2$$

Thus, the droplet volume probability density function $f(v)$ can be obtained according to the characteristics of the lognormal distribution.

Block S5, the computer device counts a number j of negative droplets or a number n−j of positive droplets among the n droplets.

In one embodiment, the number j of negative droplets or the number n−j of positive droplets included in the droplet system may be determined based on a droplet signal threshold determination algorithm according to the droplet image.

Specifically, each droplet can be judged as a positive droplet or a negative droplet according to whether each droplet includes the template to be tested (i.e., the target molecules), and then the number j of negative droplets or the number n−j of positive droplets can be counted.

In one implementation, a relative light intensity (droplet relative intensity) $I_{Rela}$ of each droplet may be calculated first. When the relative light intensity $I_{Rela}$ of any droplet is greater than a preset threshold, the computer device may determine that the any droplet includes the target molecules, and determine that the any droplet is a positive droplet. Conversely, when the relative light intensity of the any droplet is less than or equal to the preset threshold, it is determined that the any droplet does not contain the target molecules, and it is determined that the any droplet is a negative droplet.

Block S6, the computer device performs quantitative analysis for the target molecules according to the total volume V of the sample containing the target molecules, the total number n of droplets in the droplet system, the droplet volume distribution of the droplet system, the number j of negative droplets or the number n−j of positive droplets of the droplet system.

In one embodiment, the performing of the quantitative analysis of the target molecules includes, but not limited to, calculating a total number m of the target molecules, and calculating a concentration of the target molecules.

In one embodiment, the performing of the quantitative analysis of the target molecules includes (c1)-(c4):

(c1) The droplet volume probability density function of the droplet system is set as $f(v;\mu,\sigma^2)$, and, $$f(v;\mu,\sigma^2)=\frac{1}{v\sigma\sqrt{2\pi}}e^{-(\ln v-\mu)^2/2\sigma^2}=\frac{1}{v\times\sqrt{2\pi\times D[v]}}e^{-(\ln v-E[v])^2/(2\times D[v])};$$

Wherein v represents the volume of the droplet, μ represents the expectation, and a represents the standard deviation; E[v] represents the expectation of the droplet volume distribution of the droplet system; D[v] represents the variance of the droplet volume distribution of the droplet system.

(c2) A functional relationship between a probability p(v) of each droplet being a negative droplet and the volume v of each droplet satisfies $p(v)=e^{-mv/V}$, where V represents the total volume of the sample containing the target molecules, and m represents the total number of the target molecules.

(c3) An integral expression $f(v;\mu,\sigma^2)dv$ of the droplet volume probability density function $f(v;\mu,\sigma^2)$ of the droplet system in a volume interval [0, ∞], is expressed as a proportion of a number of droplets each with a volume v in the n droplets, wherein an expectation of the number of droplets each with the volume v is $nf(v;\mu,\sigma^2)dv$, and an expectation of the number of negative droplets each with the volume v is $np(v)f(v;\mu,\sigma^2)dv$, a range of v is [0,∞], $np(v)f(v;\mu,\sigma^2)dv$ is integrated in the volume interval of each droplet of all droplets (i.e., the n droplets) to obtain the expectation of the number $C_0$ of the negative droplets in all droplets as:

$$E[C_0]=\int_0^\infty np(v)f(v;\mu,\sigma^2)dv=\int_0^\infty ne^{-mv/V}\times f(v;\mu,\sigma^2)dv.$$

(c4) Taking the value of the number j of negative droplets as the value of $E[C_0]$, thereby calculating the total number i of the target molecules; and obtaining a concentration of the target molecules according to the total volume V of the sample containing the target molecules and the total number m of the target molecules.

In this embodiment, in order to verify the feasibility of the method for analyzing droplets based on volume distribution provided in this application, three examples are provided below to verify the feasibility of the method for analyzing droplets based on volume distribution provided in this application authenticating.

Example 1: A Verification Using Simulation-Based Quantitative Algorithm

Figure 6:
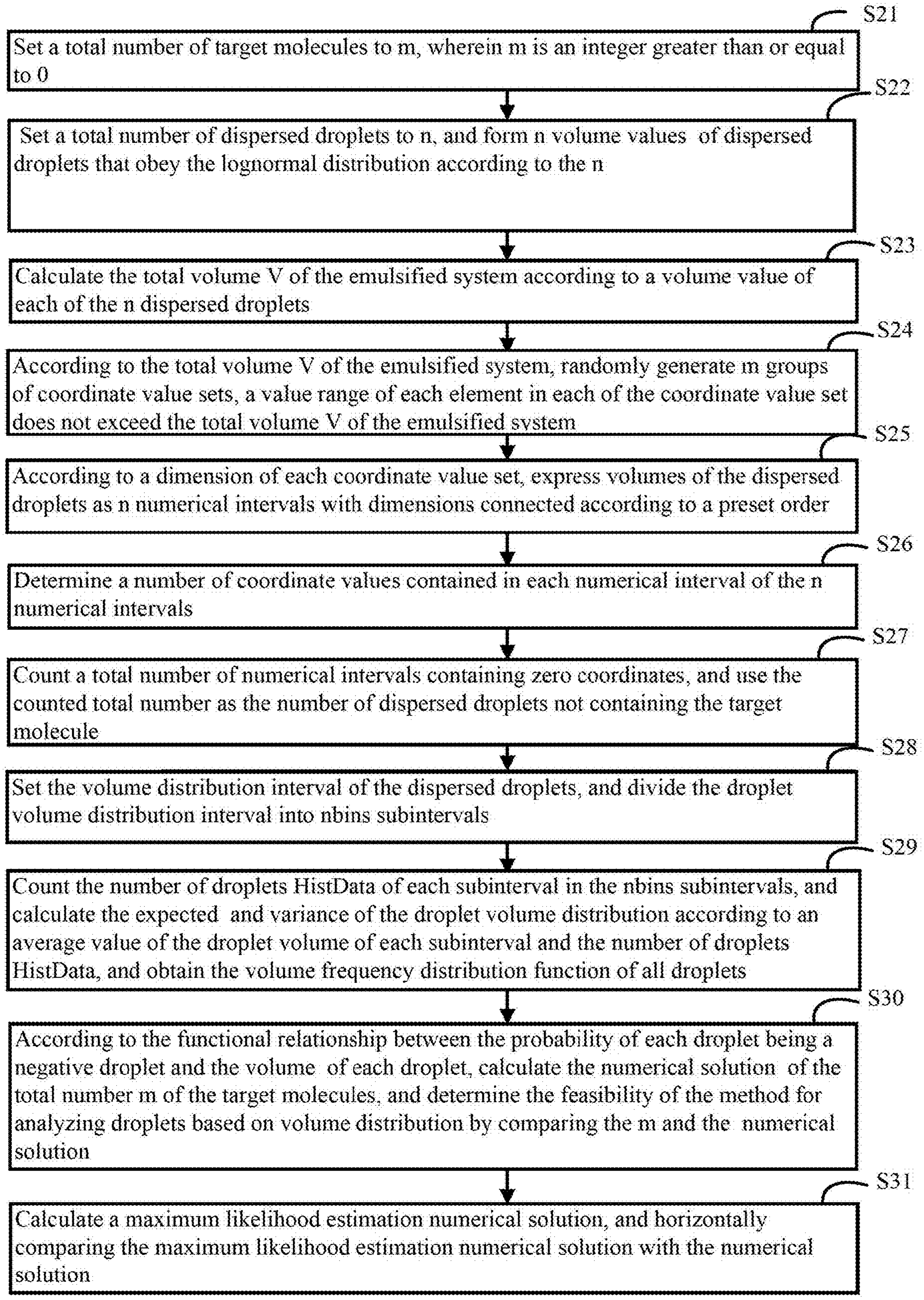
FIG. 6 is a flowchart illustrating a feasibility of the droplet analysis method verified by a simulation-based quantitative algorithm.

Specifically, it is a verification method for digital amplification absolute quantitative detection based on simulated implementation of dispersed droplets that obey the lognormal distribution. The verification method is applied to a computer device. The blocks are shown in FIG. 6.

Block S21, setting a total number of target molecules to m, wherein m is an integer greater than or equal to 0.

Block S22, setting a total number of dispersed droplets to n, and forming n volume values $v_i$ of dispersed droplets that obey the lognormal distribution according to the n, wherein, $v_i$ represents a volume of the ith dispersed droplet, i=1, 2, 3, . . . , n, wherein, n is an integer greater than 1.

Block S23, calculating the total volume V of the emulsified system according to a volume value $v_i$ of each of the n dispersed droplets.

Block S24, according to the total volume V of the emulsified system, randomly generating m groups of coordinate value sets, wherein a value range of each element in each of the coordinate value set does not exceed the total volume V of the emulsified system.

Block S25, according to a dimension of each coordinate value set, expressing volumes of the dispersed droplets as n numerical intervals with dimensions connected according to a preset order.

Block S26, determining a number of coordinate values contained in each numerical interval of the n numerical intervals.

Block S27, counting a total number of numerical intervals containing zero coordinates, and using the counted total number as the number $C_0$ of dispersed droplets not containing the target molecules.

Block S28, setting the volume distribution interval of the dispersed droplets, taking the volume $v_{min}$ of the smallest droplet and the volume $v_{max}$ of the largest droplet among the n dispersed droplets as the upper boundary and the lower boundary respectively, thereby determining the volume distribution interval of the dispersed droplets, determining the number of divisions nbins, and divide the droplet volume distribution interval into nbins subintervals according to a certain division method (such as a method of average division, a method of logarithmic division, or a method of artificial settings, etc.).

Block S29, counting the number of droplets HistData of each subinterval in the nbins subintervals, and calculating the expectation E[v] and variance D[v] of the droplet volume distribution according to an average value of the droplet volume of each subinterval and the number of droplets HistData. According to the expectation E[v] and variance D[v] of the droplet volume distribution, the volume frequency distribution function (v) of all droplets is obtained.

Block S30, according to the functional relationship $p(v)=e^{-mv/V}$ between the probability p(v) of each droplet being a negative droplet and the volume v of each droplet, calculating the numerical solution $M_{Log\ N}$ of the total number m of the target molecules. Compare whether a difference between the m and the $M_{Log\ N}$ is within a preset error range, and if the difference is within the preset error range, then determine the method for analyzing droplets based on volume distribution can be used for quantitative analysis of target molecules.

Block S31, calculating a maximum likelihood estimation numerical solution $M_{C_0}$ or $M_{MLE}$ of the total number m of target molecules according to anyone of the following two formulas, and comparing $M_{C_0}$ or $M_{MLE}$ with $M_{Log\ N}$ horizontally. Wherein, when $M_{Log\ N}$ is close to $M_{C_0}$ or $M_{Log\ N}$ is close to $M_{MLE}$, it means that the method for analyzing droplets based on volume distribution provided by the present application is feasible.

$$E[C_0] = \sum_{i=1}^{n} e^{-mv_i/\sum_{i=1}^{n} v_i} \sum_{p=1}^{n-j} \frac{v_p \times e^{-mv_p/\sum_{i=1}^{n} v_i}}{\sum_{i=1}^{n} v_i \times \left(1 - e^{-mv_p/\sum_{i=1}^{n} v_i}\right)} = \sum_{q=1}^{j} \left( v_q \Big/ \sum_{i=1}^{n} v_i \right)$$

Wherein, n represents the total number of droplets (n is an integer greater than 1), the volumes of the n droplets are respectively represented by $v_i$, i=1, 2, 3, . . . , n, the number of negative droplets is represented by j, the volumes of the negative droplets are respectively represented by $v_q$, q=1, 2, 3, . . . , j, and the volumes of the positive droplets are respectively represented by $v_p$, p=1, 2, 3, . . . , n−j.

It should be noted that since both blocks S30 and S31 are used to determine whether the method for analyzing droplets based on volume distribution provided in this application can be used for quantitative analysis of target molecules, in other embodiments, it may not include block S31.

Figure 7:
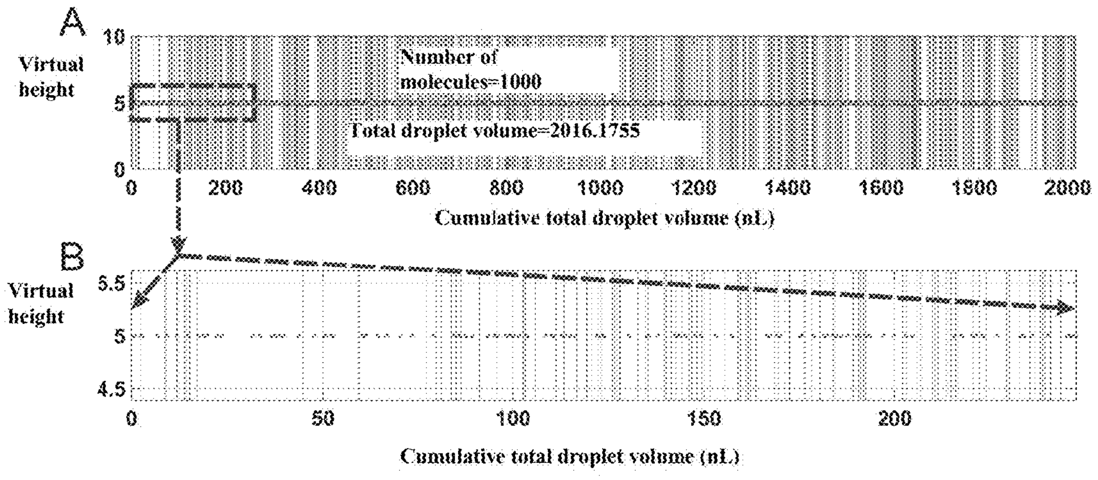
FIG. 7 shows a schematic diagram of a droplet volume range and molecular coordinates contained generated by a single simulation.
Figure 8:
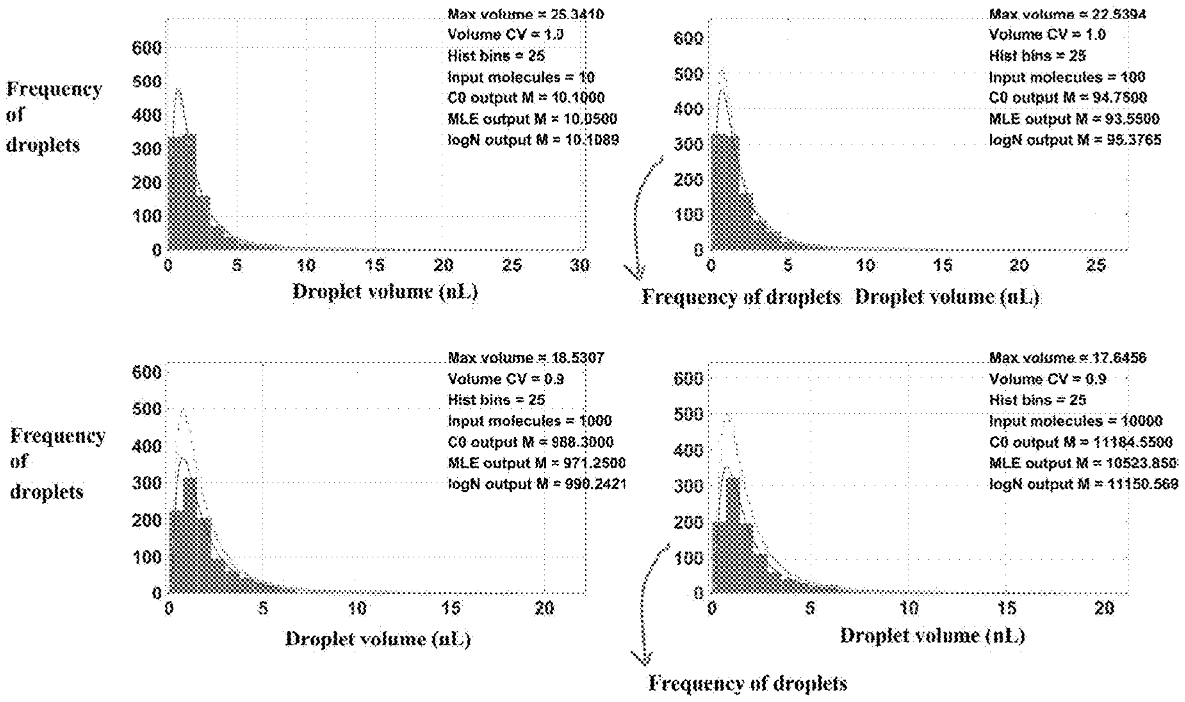
FIG. 8 shows simulation results of setting the total number of target molecules m to different values respectively and a maximum likelihood estimation numerical solution $M_{C_0}$ or $M_{MLE}$ is side-by-side compared with the numerical solution $M_{Log\ N}$ based on the lognormal distribution of droplet volumes.

The verification method provided in this application can be clearly understood in conjunction with FIG. 7, the following table and FIG. 8. FIG. 7 is a schematic diagram of the droplet volume range and molecular coordinates generated by a single simulation. A in FIG. 7 shows the molecular coordinate position distribution between the droplet volume range from 0 to 2016.1755. B in FIG. 7 shows the partial enlargement of the volume interval. The following table shows the droplet volume and molecular coordinate data generated by the simulation. FIG. 8 shows the simulation results and maximum likelihood estimation values of setting the number of droplets to 1024, the number of sub-intervals divided by the volume distribution interval nbins is 25; setting the total number of target molecules m to 10, 100, 1000 and 10000 respectively and the maximum likelihood estimation numerical solution $M_{C_0}$ or $M_{MLE}$ is horizontally compared with the numerical solution $M_{Log\ N}$ based on the lognormal distribution of droplet volumes.

| Total number of droplets n | Droplet volume $v_i$ | Number of molecules in the droplet | Total number of molecules m | Molecular coordinates |
|---|---|---|---|---|
| 1024 | 2.212694152 | 1 | 1000 | 459.1090318 |
| Total volume of droplets | 6.510283577 | 4 | Minimum coordinate of molecular | 1621.91158 |
| 2016.175548 | 0.215662675 | 0 | 0.688447775 | 1988.15926 |
| Minimum volume $v_{min}$ | 2.899040916 | 2 | Maximum coordinate of molecular | 60.46903677 |
| 0.095916776 | 1.844047826 | 0 | 2015.122819 | 1079.993043 |
| Maximum volume $v_{max}$ | 0.476090017 | 0 | | 175.5629616 |
| 27.82081448 | 0.985687958 | 1 | | 1617.15715 |
| Average volume | 1.881044429 | 0 | | 1994.28978 |
| 1.968921434 | 27.82081448 | 13 | | 134.9754092 |
| Standard deviation of volume | 14.18636312 | 5 | | 1893.992007 |
| 2.216300426 | 0.45965411 | 0 | | 36.64909884 |
| Coefficient of volume variation | 17.6955486 | 7 | | 1378.738692 |
| 1.125641881 | 2.587034458 | 1 | | 1580.150327 |
| | 1.341887178 | 0 | | 1076.915104 |
| | 2.564173208 | 0 | | 1785.040076 |
| | 1.192352389 | 1 | | 1812.551695 |
| | 1.275344886 | 2 | | 1262.000136 |
| | 4.888219872 | 2 | | 277.9680913 |
| | . . . | . . . | | . . . |
| | . . . | . . . | | |

Figure 9:
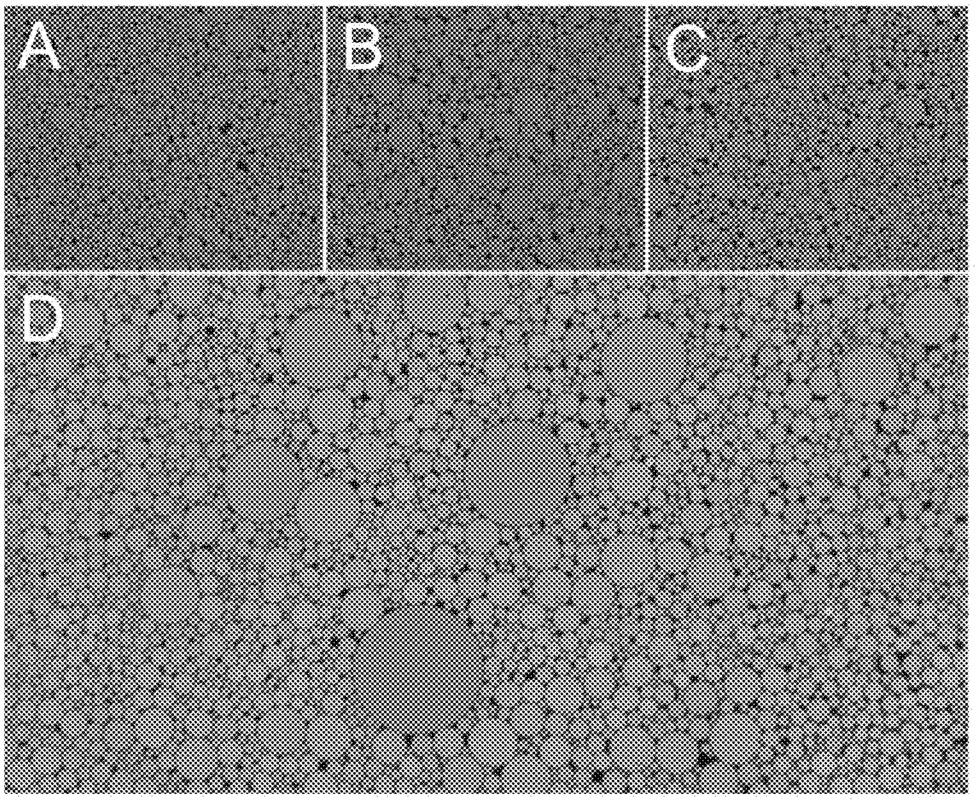
FIG. 9 shows an image of random emulsified droplets loaded into a sequencing chip.
Figure 10:
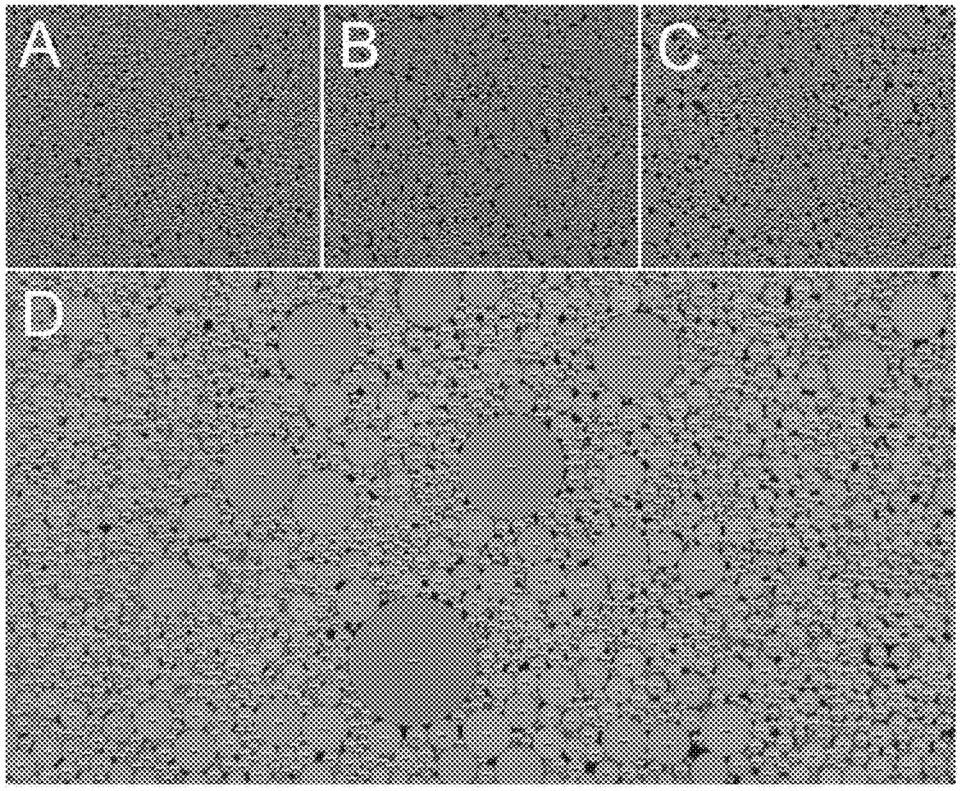
FIG. 10 is a schematic diagram of extracting droplets data from the image of random emulsified droplets.
Figure 11:
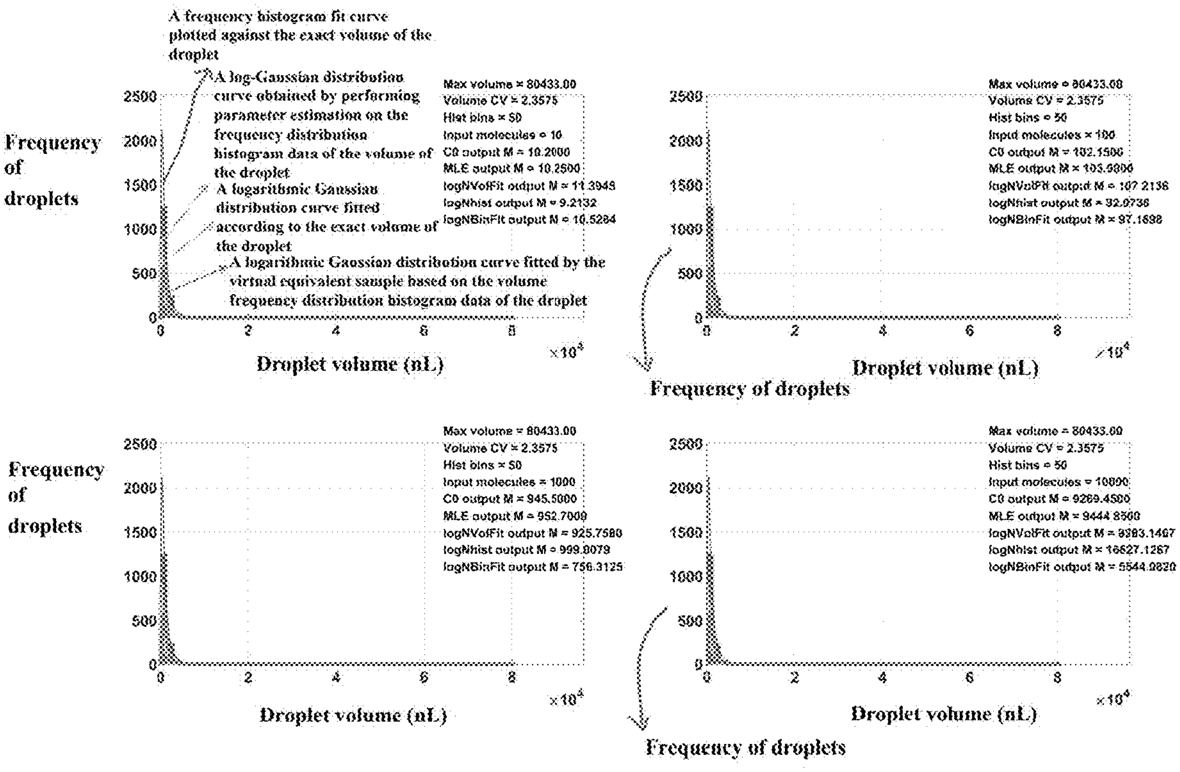
FIG. 11 shows the simulation results of setting the total number of target molecules m to different values respectively and a maximum likelihood estimation numerical solution $M_{C_0}$ or $M_{MLE}$ is side-by-side compared with the numerical solution $M_{Log\ N}$ based on the lognormal distribution of droplet volumes.

Example 2: A Verification Method of Experimental Simulation Based on Random Emulsified Droplets Specifically, in this example, a certain concentration of fluorescent dye (such as 25 μM calcein) solution is vortexed to form random emulsified dispersed droplets, and then is loaded into the sequencing chip channel to form a quasi-two-dimensional droplet plane. Fluorescent images of the droplets are acquired on the microscopic imaging device. By processing and analyzing the fluorescence images, the relevant data information of the droplets is obtained, and the feasibility of the method for analyzing the droplets based on the volume distribution proposed in this application is calculated and verified. The process of this embodiment is similar to that of Example 1, except that the data about the droplets in blocks 22-23 include the number n of droplets, the volume of droplets $v_i$ (including the minimum volume $v_{min}$ and the maximum volume $v_{max}$), and the total volume of emulsified droplets V is calculated by processing and analyzing the fluorescence image acquired in the experiment. However, the droplet data in Example 1 is simulated by random numbers subject to lognormal distribution. The specific experimental data and simulation data results are shown in FIG. 9 to FIG. 11. Among them, FIG. 9 schematically shows the image of random emulsified droplets loaded into the sequencing chip. FIG. 10 is a schematic diagram of extracting droplet data information from an image of random emulsified droplets. FIG. 11 shows that the number of droplets is 1595, the coefficient of volume variation is 2.3575, and the number of subintervals nbins of the volume distribution interval is 50; the total number of target molecules m is set to be 10, 100, 1000 and 10000 respectively, and the maximum likelihood estimation numerical solution $M_{C_0}$ or $M_{MLE}$ is horizontally compared with the numerical solution $M_{Log\ N}$ based on the lognormal distribution of droplet volumes.

Example 3: A Validation Method for Digital Loop-Mediated Isothermal Amplification Experiments Based on Random Emulsified Droplets In this example, a digital isothermal amplification experiment method is adopted, and a loop-mediated isothermal amplification solution containing a certain concentration of nucleic acid template is vortexed to form random emulsified dispersed droplets, and then loaded into a quasi-two-dimensional droplet plane is formed in the channel of the sequencing chip, and the temperature conditions required for amplification are applied to the chip for one hour. After completion, the fluorescent image of the droplets in the chip is obtained on a microscopic imaging device. By processing and analyzing the fluorescence image, the relevant data information of the droplets is obtained, and the feasibility of the method for analyzing the droplet based on the volume distribution proposed in this application is calculated and verified. Specifically, prepare the mixed liquid of the system to be emulsified according to the formula in the following table:

| | |
|---|---|
| 10 × Isothermal Amplification Buffer ( NEB company) | 2.5 μL |
| 5M betaine (BBI company) | 5 μL |
| 100 mM $MgSO_4$ (NEB company) | 1.5 μL |
| 100 mM dNTPs mix (NEB company) | 3.5 μL |
| 10 μM F3&B3 ( Sangon Biotech company) | 1 μL |
| 10 μM FIP&BIP (Sangon Biotech company) | 6 μL |

-continued

| | |
|---|---|
| 40 μM LF&LB (Sangon Biotech company) | 0.5 μL |
| 20 mg/ml BSA (BBI company) | 1 μL |
| 1 U/μl UDG (NEB company) | 0.5 μL |
| 8 U/μl Bst 2.0 WarmStart DNA polymerase (NEB company) | 1 μL |
| 250 mM SYTO-9 (Invitrogen company) | 0.5 μL |
| 50 × ROX ( Invitrogen company) | 0.5 μL |
| LAMP template ( Synthetic DNA fragment of toxr gene of vibrio riverina) | 1.5 μL |
| Total volume | 25 μL |

Mix the above mixed solution and let it stand at room temperature for 5 minutes. Take the mixed solution and emulsifier and mix according to a volume ratio of 1:10. Mixing method: performing manual oscillation or vortex oscillation for twice, each time for 3 seconds, to form a random emulsification system of multi-volume droplets. The added two dyes, i.e., SYTO-9 is the working dye, and ROX is the reference dye. Load the emulsification system onto the BGISEQ-500 chip, seal the injection hole and the outlet hole at both ends with PCR sealing film, transfer the chip to a water bath for heating, and set the temperature to 67 degrees Celsius. After fully reacting for one hour, the chip was taken out and placed under an Olympus SZX16 stereo fluorescence microscope to take images of the chip. Fluorescence excitation and emission were performed at 480 nm/535 nm and 540 nm/605 nm respectively, and fluorescence images of two dye channels of SYTO-9 and ROX were taken.

Figure 12:
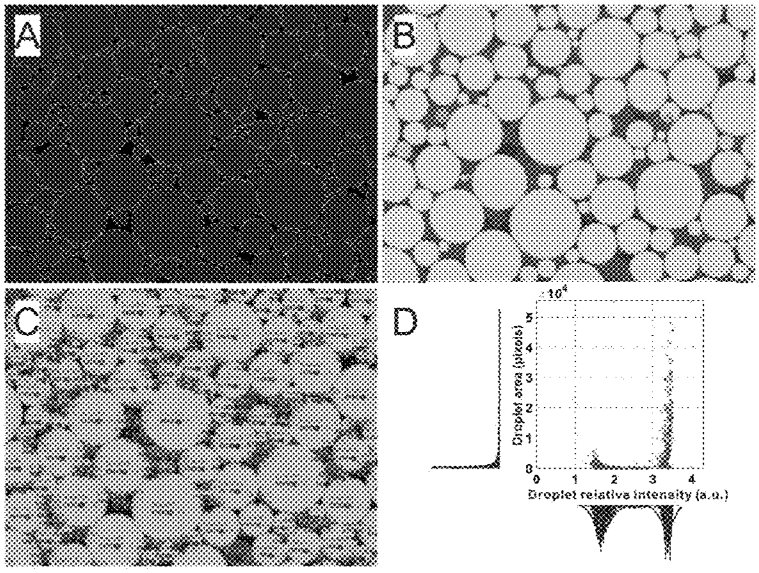
FIG. 12 schematically shows the image processing of the quasi-two-dimensional droplet fluorescence microscopy and digital isothermal amplification assay based on the MGI sequencing chip.

A background correction operation of photometric inhomogeneity is performed on the fluorescence images of these two channels respectively, and images with uniform backgrounds can be obtained. The background-corrected image of the reference dye channel is enhanced and is denoised using a block-matching three-dimensional filter denoising (BM3D) algorithm, and a noise-reduced image of the reference dye channel is obtained. The noise-reduced image of the reference dye channel is read, and a watershed segmentation line of a grayscale terrain image is obtained by using a watershed dam method, so as to segment adjacent droplet areas in the image. Use a bwlabel method to mark each different region with a different label value. With the image of the reference dye channel after background correction as a fixed reference, a secondary registered image is obtained by correcting the image of the working dye channel using a secondary registration method, and at the same time, fill an uneven edge of the secondary registered image with a foreground color. Read the secondary registered image and each label value marking each different region, calculate an average light intensity $I_{Abs}$ of each region on the secondary registered image according to the each label value, and similarly according to the each label value, calculate an average light intensity $I_{Ref}$ of each region on the background-corrected image of the reference dye channel, and then calculate a relative light intensity $I_{Rela}=I_{Abs}/I_{Ref}$ of each region, i.e., each droplet. Calculate a total number of pixels in each region according to the label value, and then determine an image magnification and calculate the volume of each droplet. In addition, according to the relative average light intensity of each droplet, a state of each droplet after reaction and related content information of each droplet are judged, and the droplets are classified accordingly. Further, the quantitative results of the inclusions were calculated according to the total number of droplets, the volume of each droplet and the classification results. The droplets obtained after the secondary registration can be divided into negative droplets and positive droplets according to the relative light intensity. The specific blocks and results are shown in FIG. 12. FIG. 12 schematically shows the image processing of the quasi-two-dimensional droplet fluorescence microscopy and digital isothermal amplification assay based on the MGI sequencing chip. Records of application numbers PCT/CN2019/122068 and PCT/CN2020/075309 can be used as references.

According to the above processing and analysis of the fluorescence images, the relevant data information of the droplets is obtained, and the number n of all the droplets is counted, and each droplet is judged as a negative droplet or a positive droplet according to the threshold value of the light intensity signal, and count the number of droplets. According to the droplet image, the minimum volume $v_{min}$ and the maximum volume $v_{max}$ of the droplets are determined, thereby determining the droplet volume distribution interval $[v_{min}, v_{max}]$. According to the total volume V of the system before emulsification (for example, 25 μL) and the total number of droplets n, the average droplet volume E[v]=V/n can be obtained. The drop volume distribution interval $[v_{min}, v_{max}]$ is divided into 25 subintervals on average, and the subintervals that each droplet falls into are determined one by one, and the frequency of droplet occurrence in the 25 subintervals is counted, and the variance D[v] of the droplet volume distribution is obtained according to the embodiment 1. According to the law of the lognormal distribution, E[v] and D[v] are respectively used as the expectation and variance of the distribution function f(v), and the numerical solution $M_{Log\ N}$ (unit: copy) of the total number of molecules m to be measured in the droplet system is calculated according to the following formula, so as to calculate the concentration of the molecule to be tested as $M_{Log\ N}/V$ (unit: copy/mL).

$$f(v;\mu,\sigma^2)=\frac{1}{v\sigma\sqrt{2\pi}}e^{-(\ln v-\mu)^2/2\sigma^2}=\frac{1}{v\times\sqrt{2\pi\times D[v]}}e^{-(\ln v-E[v])^2/(2\times D[v])}$$

$$E[C_0]=\int_0^\infty np(v)f(v;\mu,\sigma^2)dv=\int_0^\infty ne^{-m/V}\times f(v;\mu,\sigma^2)dv.$$

Among them, v represents the droplet volume, μ represents the expectation value, and σ represents the standard deviation; V represents the total volume of the system before emulsification, and m represents the total number of target molecules.

Referring to FIG. 13, it is a diagram of an operating environment of the droplet analysis system provided by the preferred embodiment of the present application.

In this embodiment, a droplet analysis system 30 runs in a computer device 3 and is used to analyze the droplets based on images, such as analyzing a relative light intensity of each of the droplets. In this embodiment, the computer device 3 includes, but is not limited to, a storage device 31, a processor 32, and at least one communication bus 33.

Those skilled in the art should understand that the structure of the computer device shown in FIG. 3 does not constitute a limitation of the embodiment of the present application, it can be a bus structure or a star structure, and the computer device 3 may also include more or less other hardware or software than shown, or have a different arrangement of components. In some embodiments, the computer device 3 includes a terminal capable of automatically performing numerical calculations and/or information processing according to preset or stored computer-readable instructions, and its hardware includes but not limited to microprocessors, dedicated Integrated circuits, programmable gate arrays, digital processors and embedded devices, etc.

It should be noted that the computer device 3 is only an example, and other existing or future computer devices that can be adapted to this application should also be included in the scope of protection of this application, and are included here by reference.

In some embodiments, the storage device 31 is used to store program codes and various data, such as the droplet analysis system 30 installed in the computer device 3, and realize high-speed, automatic Complete program or data access. The storage device 31 includes a read-only memory (ROM), a programmable read-only memory (PROM), an erasable programmable read-only memory (EPROM), one-time programmable read-only memory (OTPROM), electronically erasable programmable read-only memory (EEPROM), compact disc read-only memory (CD-ROM) or other optical disk storage, magnetic disk storage, tape storage, or any other non-volatile readable storage medium that can be used to carry or store data. In some embodiments, the at least one processor 32 may be composed of an integrated circuit. For example, the at least one processor 32 can be composed of a single packaged integrated circuit or can be composed of multiple packaged integrated circuits with the same function or different function.

The at least one processor 32 includes one or more central processing units (CPUs), one or more microprocessors, one or more digital processing chips, one or more graphics processors, and various control chips. The at least one processor 32 is a control unit of the computer device 3. The at least one processor 32 uses various interfaces and lines to connect various components of the computer device 3, and executes programs or modules or instructions stored in the storage device 31, and invokes data stored in the storage device 31 to perform various functions of the computer device 3 and to process data, for example, to perform a function of analyzing droplets based on their volume distribution (As shown in FIG. 1).

In some embodiments, the at least one communication bus 33 is configured to implement a communication connection between the storage device 31 and the at least one processor 32, and the like.

Although not shown, the computer device 3 may also include a power supply (such as a battery) for supplying power to each component. Preferably, the power supply may be logically connected to the at least one processor 32 through a power management device, thereby realizing manage functions such as charging, discharging, and power management. The power supply may also include one or more DC or AC power supplies, recharging devices, power failure detection circuits, power converters or inverters, power status indicators and other arbitrary components. The computer device 3 may also include various sensors, Bluetooth modules, Wi-Fi modules, etc., which will not be repeated here.

It should be understood that the embodiments are only for illustration, and are not limited by the structure in the scope of the patent application.

In some embodiments, the droplet analysis system 30 may include a plurality of functional modules composed of segments of program codes. The program codes of each segment in the droplet analysis system 30 can be stored in a storage device (such as the storage device 31 of the computer device 3), and executed by at least one processor (such as the processor 32), so as to realize the function of analyzing droplets based volume distribution (as shown in FIG. 1).

In this embodiment, the droplet analysis system 30 can be divided into a plurality of functional modules according to functions it performs. The function modules may include: an acquisition module 301 and an execution module 302. The module referred to in this application refers to a series of segments of computer-readable instructions that can be executed by at least one processor (such as the processor 32) and can complete fixed functions, which are stored in the storage device (such as the storage device 31 of the computer device 3).

The acquisition module 301 obtains the total volume V of the sample containing target molecules. When the system to be emulsified is emulsified into droplets, conditions and operations required for the execution of the amplification reaction are performed on the droplets, and the droplet system is obtained when the droplets containing the sample fully executing the amplification reaction. The execution module 302 acquires droplet image of the droplet system, and obtains the total number n of droplets comprised in the droplet system based on the droplet image. The execution module 302 obtains droplet volume distribution of the droplet system based on the droplet image; and counting the number j of negative droplets or the number n−j of positive droplets among the n droplets. The execution module 302 performs the quantitative analysis for the target molecules according to the total volume V of the sample containing the target molecules, the total number n of droplets, the droplet volume distribution, and the number j of negative droplets or the number n−j of positive droplets.

In this embodiment, the integrated units implemented in the form of software function modules may be stored in a non-volatile readable storage medium. The above-mentioned software functional modules include several computer-readable instructions to enable a computer device or processor to execute part of methods of various embodiments of the present application, such as the method for analyzing droplets based on volume distribution shown in FIG. 1.

In a further embodiment, referring to FIG. 12, the at least one processor 32 can execute an operating device of the computer device 3 and various installed applications (such as the droplet analysis system 30), program codes, etc., for example, the various modules mentioned above.

Program codes are stored in the storage device 31, and the at least one processor 32 can invoke the program codes stored in the storage device 31 to execute related functions. For example, the various modules of the droplet analysis system 30 in FIG. 3 are program codes stored in the storage device 31 and executed by the at least one processor 32, so as to realize the functions of the various modules to achieve a function of analyzing droplets based on volume distribution (see description of FIG. 1 for details).

In one embodiment of the present application, the storage device 31 stores a plurality of computer-readable instructions, and the plurality of computer-readable instructions are executed by the at least one processor 32 to achieve the purpose of analyzing droplets based on volume distribution. Specifically, for a specific implementation method of the at least one processor 32 for the above computer-readable instructions, refer to the description of FIG. 1 for details.

It should be noted that, in the several embodiments provided in this application, it should be understood that the disclosed non-volatile readable storage medium, device and method may be implemented in other ways. For example, device embodiments described above are only illustrative. For example, the division of the modules is only a logical function division, and there may be other division methods in actual implementation.

The modules described as separate components may or may not be physically separated, and the components shown as modules may or may not be physical units, that is, they may be located in one place, or may be distributed to multiple network units. Part or all of the modules can be selected according to actual needs to achieve the purpose of the solution of this embodiment.

In addition, each functional module in each embodiment of the present application may be integrated into one processing unit, each unit may exist separately physically, or two or more units may be integrated into one unit. The above-mentioned integrated units can be implemented in the form of hardware, or in the form of hardware plus software function modules.

It will be apparent to those skilled in the art that the present application is not limited to the details of the exemplary embodiments described above, but that the present application can be implemented in other specific forms without departing from the spirit or essential characteristics of the present application. Therefore, the embodiments should be regarded as exemplary and not restrictive in all points of view, and the scope of the application is defined by the appended claims rather than the foregoing description, and it is intended that the scope of the present application be defined by the appended claims rather than by the foregoing description. All changes within the meaning and range of equivalents of the elements are embraced in this application. Any reference sign in a claim should not be construed as limiting the claim concerned. Furthermore, it is clear that the word "comprising" does not exclude other elements or the singular does not exclude the plural. A plurality of units or means stated in the device claims may also be realized by one unit or device through software or hardware. The words first, second, etc. are used to denote names and do not imply any particular order.

Finally, it should be noted that the above embodiments are only used to illustrate the technical solutions of the present application without limitation. Although the present application has been described in detail with reference to the preferred embodiments, those skilled in the art should understand that the technical solutions of the present application can be Make modifications or equivalent replacements without departing from the spirit and scope of the technical solutions of the present application.

What is claimed is:

1. A method for analyzing droplets based on volume distribution, comprising:

preparing a system to be emulsified using a sample containing target molecules, and obtaining a total volume V of the sample containing the target molecules;

emulsifying the system into droplets, subjecting the droplets to conditions and operations for performing amplification reactions, causing the droplets containing the sample to undergo amplification reactions and obtaining a droplet system;

acquiring a droplet image of the droplet system using a fluorescence microscope, and obtaining a total number n of droplets comprised in the droplet system based on the droplet image;

obtaining a droplet volume distribution of the droplet system based on the droplet image, wherein the droplet volume distribution of the droplet system comprises a droplet volume cumulative distribution function, a droplet volume probability density function, and/or an expectation and a variance of a droplet volume distribution;

counting a number j of negative droplets or a number n−j of positive droplets among the n droplets; and performing a quantitative analysis for the target molecules according to the total volume V of the sample containing the target molecules, the total number n of droplets, the droplet volume distribution, and the number j of negative droplets or the number n−j of positive droplets;

wherein performing the quantitative analysis for the target molecules comprises:

setting the droplet volume probability density function of the droplet system as $f(v;\mu,\sigma^2)$, wherein, $$f(v;\mu,\sigma^2)=\frac{1}{v\sigma\sqrt{2\pi}}e^{-(\ln v-\mu)^2/2\sigma^2}=\frac{1}{v\times\sqrt{2\pi\times D[v]}}e^{-(\ln v-E[v])^2/(2\times D[v])};$$

wherein v represents a volume of the droplet, μ represents an expectation, and σ represents a standard deviation; E[v] represents an expectation of the droplet volume distribution of the droplet system; D[v] represents a variance of the droplet volume distribution of the droplet system;

a functional relationship between a probability p(v) of each droplet is a negative droplet and a volume v of each droplet satisfies $p(v)=e^{-mv/V}$, where V represents the total volume of the sample containing the target molecules, and m represents the total number of the target molecules;

expressing an integral expression $f(v;\mu,\sigma^2)dv$ of the droplet volume probability density function $f(v;\mu,\sigma^2)$ of the droplet system in a volume interval [0,∞], as a proportion of a number of droplets each with a volume v in the n droplets, wherein an expectation of the number of droplets each with the volume v is $nf(v;\mu,\sigma^2)dv$, and an expectation of the number of negative droplets each with the volume v is $np(v)f(v;\mu,\sigma^2)dv$, a range of v is [0,∞], $np(v)f(v;\mu,\sigma^2)dv$ is integrated in the volume interval of each droplet of the n droplets to obtain the expectation of the number $C_0$ of the negative droplets in the n droplets as:

$$E[C_0]=\int_0^\infty np(v)f(v;\mu,\sigma^2)dv=\int_0^\infty ne^{-\frac{mv}{V}}\times f(v;\mu,\sigma^2)dv;$$

taking a value of the number j of negative droplets as a value of $E[C_0]$, thereby calculating a total number m of the target molecules; and obtaining a concentration of the target molecules according to the total volume V of the sample containing the target molecules and the total number m of the target molecules.

2. A computer device, comprising:

a storage device and a processor, the storage device storing at least one computer-readable instruction, the processor executing the at least one computer-readable instruction to implement following functions:

obtaining a total volume V of a sample containing target molecules;

acquiring a droplet image of a droplet system using a fluorescence microscope, and obtaining a total number n of droplets comprised in the droplet system based on the droplet image, wherein the droplet system is obtained by preparing a system to be emulsified using the sample containing target molecules; emulsifying the system into droplets; and subjecting the droplets to conditions and operations for performing amplification reactions, causing the droplets containing the sample to undergo amplification reactions;

obtaining a droplet volume distribution of the droplet system based on the droplet image, wherein the droplet volume distribution of the droplet system comprises a droplet volume cumulative distribution function, a droplet volume probability density function, and/or an expectation and a variance of a droplet volume distribution;

counting a number j of negative droplets or a number n−j of positive droplets among the n droplets; and performing a quantitative analysis for the target molecules according to the total volume V of the sample containing the target molecules, the total number n of droplets, the droplet volume distribution, and the number j of negative droplets or the number n−j of positive droplets;

wherein performing the quantitative analysis for the target molecules comprises:

setting the droplet volume probability density function of the droplet system as $f(v;\mu,\sigma^2)$, wherein, $$f(v;\mu,\sigma^2)=\frac{1}{v\sigma\sqrt{2\pi}}e^{-(\ln v-\mu)^2/2\sigma^2}=\frac{1}{v\times\sqrt{2\pi\times D[v]}}e^{-(\ln v-E[v])^2/(2\times D[v])};$$

wherein v represents a volume of the droplet, μ represents an expectation, and σ represents a standard deviation; E[v] represents an expectation of the droplet volume distribution of the droplet system; D[v] represents a variance of the droplet volume distribution of the droplet system;

a functional relationship between a probability p(v) of each droplet is a negative droplet and a volume v of each droplet satisfies $p(v)=e^{-mv/V}$, where V represents the total volume of the sample containing the target molecules, and m represents the total number of the target molecules;

expressing an integral expression $f(v;\mu,\sigma^2)dv$ of the droplet volume probability density function $f(v;\mu,\sigma^2)$ of the droplet system in a volume interval [0,∞], as a proportion of a number of droplets each with a volume v in the n droplets, wherein an expectation of the number of droplets each with the volume v is $nf(v;\mu,\sigma^2)dv$, and an expectation of the number of negative droplets each with the volume v is $np(v)f(v;\mu,\sigma^2)dv$, a range of is [0,∞], $np(v)f(v;\mu,\sigma^2)dv$ is integrated in the volume interval of each droplet of the n droplets to obtain the expectation of the number $C_0$ of the negative droplets in the n droplets as:

$$E[C_0]=\int_0^\infty np(v)f(v;\mu,\sigma^2)dv=\int_0^\infty ne^{-\frac{mv}{V}}\times f(v;\mu,\sigma^2)dv;$$

taking a value of the number j of negative droplets as a value of $E[C_0]$, thereby calculating a total number m of the target molecules; and obtaining a concentration of the target molecules according to the total volume V of the sample containing the target molecules and the total number m of the target molecules.

3. A non-transitory storage medium having at least one computer-readable instruction stored thereon, and the at least one computer-readable instruction being executed by a processor, to implement following functions:

obtaining a total volume V of a sample containing target molecules;

acquiring a droplet image of a droplet system using a fluorescence microscope, and obtaining a total number n of droplets comprised in the droplet system based on the droplet image, wherein the droplet system is obtained by preparing a system to be emulsified using the sample containing target molecules; emulsifying the system into droplets; and subjecting the droplets to conditions and operations for performing amplification reactions, causing the droplets containing the sample to undergo amplification reactions;

obtaining a droplet volume distribution of the droplet system based on the droplet image, wherein the droplet volume distribution of the droplet system comprises a droplet volume cumulative distribution function, a droplet volume probability density function, and/or an expectation and a variance of a droplet volume distribution;

counting a number j of negative droplets or a number n−j of positive droplets among the n droplets; and performing a quantitative analysis for the target molecules according to the total volume V of the sample containing the target molecules, the total number n of droplets, the droplet volume distribution, and the number j of negative droplets or the number n−j of positive droplets;

wherein the obtaining of droplet volume distribution of the droplet system based on the droplet image comprises:

acquiring a volume of each droplet based on the droplet image, and sorting the n droplets according to the volume of each droplet;

dividing the n droplets into t groups based on an arrangement sequence of the n droplets;

obtaining t volume values by obtaining a volume value of a largest droplet or obtaining a volume value of a smallest droplet in each of the t groups;

determining a quantile q based on the t, and obtaining a plurality of estimated values of expectation μ and a plurality of estimated values of variance $\sigma^2$ based on the quantile q and the t volume values;

selecting, based on a preset evaluation function, a best estimated value of the expectation μ from the plurality of estimated values of the expectation μ, and selecting a best estimated value of the variance $\sigma^2$ from the plurality of estimated values of the variance $\sigma^2$; and according to characteristics of a lognormal distribution, obtaining the droplet volume probability density function θ(v) of the droplet system based on the best estimated value of the expectation μ and the best estimated value of the variance $\sigma^2$.

* * * * *